US006465238B1

(12) United States Patent
Hanke

(10) Patent No.: US 6,465,238 B1
(45) Date of Patent: Oct. 15, 2002

(54) GENE ENCODING PHOSPHOGLUCOISOMERASE

(75) Inventor: Paul D. Hanke, Aurora, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/621,451

(22) Filed: Jul. 21, 2000

Related U.S. Application Data

(60) Provisional application No. 60/145,217, filed on Jul. 23, 1999, and provisional application No. 60/150,017, filed on Aug. 20, 1999.

(51) Int. Cl.[7] .............................. C12N 9/92; C12N 15/61
(52) U.S. Cl. ................. 435/234; 435/320.1; 435/252.3; 536/23.2
(58) Field of Search .............................. 435/234, 320.1, 435/252.3; 536/23.2

(56) References Cited

U.S. PATENT DOCUMENTS 5,631,150 A    5/1997    Harkki et al. ................ 435/105

FOREIGN PATENT DOCUMENTS

| EP | 0 733 712 A1 | 9/1996 |
| EP | 0 780 477 A1 | 6/1997 |
| EP | 1 087 015 A2 | 3/2001 |
| FR | 2 772 788 | 6/1999 |
| WO | WO 94/10325 | 5/1994 |

OTHER PUBLICATIONS

Boles, E. et al., "The role of the NAD–dependent glutamate dehydrogenase in restoring growth on glucose of a *Saccharomyces cerevisiae* phophoglucose isomerase mutant," *Eur. J. Biochem.* 217:469–477, Federation of European Biochemical Societies (1993).
González Siso, M.I. et al., "Reoxidation of the NADPH produced by the pentose phosphate pathway is necessary for the utilization of glucose by *Kluyveromyces lactis* rag2 mutants," *FEBS Lett.* 387:7–10, Federation of European Biochemical Societies (1996).
Moritz, B. et al., "Kinetic properties of the glucose–6–phosphate and 6–phosphogluconate dehydrogenases from *Corynebacterium glutamicum* and their application for predicting pentose phosphate pathway flux in vivo," *Eur. J. Biochem.* 267:3442–3452, Federation of European Biochemical Societies (Jun. 2000).
Shi, H. et al., "Effect of Modifying Metabolic Network on Poly–3–Hydroxybutyrate Biosynthesis in Recombinant *Escherichia coli*," *J. Biosci. Bioeng.* 87:666–677, Elsevier Science (Jun. 1999).
Vallino, J.J. and Stephanopoulos, G., "Carbon Flux Distributions at the Pyruvate Branch Point in *Corynebacterium glutamicum* during Lysine Overproduction," *Biotechnol. Prog.* 10:320–326, American Chemical Society and American Institute of Chemical Engineers (1994).

Vallino, J.J. and Stephanopoulos, G., "Carbon Flux Distributions at the Glucose 6–Phosphate Branch Point in *Corynebacterium glutamicum* during Lysine Overproduction," *Biotechnol. Prog.* 10:327–334, American Chemical Society and American Institute of Chemical Engineers (1994).
Walfridsson, M. et al., "Xylose–Metabolizing *Saccharomyces cerevisiae* Strains Overexpressing the TKL1 and TAL1 Genes Encoding the Pentose Phosphate Pathway Enzymes Transketolase and Transaldolase," *Appl. Environ. Microbiol.* 61:4184–4190, American Society for Microbiology (1995).
Patent Abstracts of Japan, Publication No. 09224661, published Sep. 2, 1997.
Patent Abstracts of Japan, Publication No. 09224662, published Sep. 2, 1997.
Dialog File 351, Accession No. 12615741, Derwent WPI English language abstract for FR 2 772 788 (Document AN1). (1999).
International Search Report for International Application No. PCT/US00/19914, mailed Dec. 28, 2000.
Sahm, H. et al., "Construction of L–Lysine–, L–Threonine–, or L–Isoleucine–Overproducing Strains of *Corynebacterium glutamicum*, " *Ann. N. Y. Acad. Sci.* 782:25–39, Springer Press (1996).
Voet, D. and Voet, J., *Biochemistry*, Second Edition, Voet, D. and Voet, J. eds., John Wiley & Sons, Inc., New York, NY, pp. 445, 617, and 687 (1995).
Berry, A., "Improving production of aromatic compounds in *Escherichia coli* by metabolic engineering," *TIBTECH* 14:250–256 (1996).
Flores, N. et al., "Pathway engineering for the production of aromatic compounds in *Escherichia coli*," *Nature Biotechnol.* 14:620–623 (1996).
Inbar, L. et al., "Natural–abundance $^{13}$C nuclear magnetic resonance studies of regulation and overproduction of L–lysine by *Brevibacterium flavum*," *Eur. J. Biochem.* 149:601–607 (1985).
Ishino, S. et al., "[13]C Nuclear Magnetic Resonance Studies of Glucose Metabolism in L–Glutamic Acid and L–Lysine Fermentation by *Corynebacterium Glutamicum*," *J. Gen. Appl. Microbiol.* 37:157–165 (1991).
Kinoshita, S. et al., "L–Lysine Production Using Microbial Auxotroph," *J. Gen. Appl. Microbiol.* 4:128–129 (1958).
Marx, A. et al., "Determination of the Fluxes in the Central Metabolism of *Corynebacterium glutamicum* by Nuclear Magnetic Resonance Spectroscopy Combined with Metabolite Balancing," *Biotechnol. Bioengineering* 49:111–129 (1996).

(List continued on next page.)

*Primary Examiner*—Charles L. Patterson, Jr.
(74) *Attorney, Agent, or Firm*—Sterne, Kessler, Goldstein & Fox P.L.L.C.

(57) ABSTRACT

The present invention relates, in general, to a method of producing L–amino acids comprising culturing altered bacterial cells having increased amounts of NADPH as compared to unaltered bacterial cells whereby L–amino acids yields from said altered bacterial cells are greater than yields from unaltered bacterial cells. The invention also relates to a gene encoding phosphoglucoisomerase.

10 Claims, 3 Drawing Sheets

OTHER PUBLICATIONS

Marx, A. et al., "Response of the Central Metabolism in *Corynebacterium glutamicum* to the use of an NADH–Dependent Glutamate Dehydrogenase," *Metabolic Engineering* 1:35–48 (Jan. 1999).

Walker, T.E. et al., "$^{13}$C Nuclear Magnetic Resonance Studies of the Biosynthesis by *Microbacterium ammoniaphilum* of L–Glutamate Selectively Enriched with Carbon–13," *J. Biol. Chem.* 257:1189–1195 (1982).

Swiss–Prot Accession No. P77895, Swiss Prot ID No. G6PI_MYCTU (Jul. 15, 1998).

Dominguez, H. et al., "Carbon–flux distribution in the central metabolic pathways of *Corynebacterium glutamicum* during growth on fructose," *Eur. J. Biochem.* 254:96–102 (May 1998).

Fitzpatrick, R. et al., "Construction and characterization of recA mutant strains of *Corynebacterium glutamicum* and *Brevibacterium lactofermentum*," *Appl. Microbiol. Biotechnol.* 42:575–580 (1994).

O'Gara, J.P. and L.K. Dunican, "Direct Evidence for a Constitutive Internal Promoter in the Tryptophan Operon of *Corynebacterium glutamicum*," *Biochem. & Biophys. Res. Comm.* 203:820–827 (1994).

Vallino, J.J. and G. Stephanopoulos, "Metabolic Flux Distributions in *Corynebacterium glutamicum* During Growth and Lysine Overproduction," *Biotechnol. & Bioengineering* 41:633–646 (1993).

Cocaign–Bousquet, M. and Lindley, N.D., "Pyruvate overflow and carbon flux within the central metabolic pathways of *Corynebacterium glutamicum* during growth on lactate," *Enzyme Microb. Tech.* 17:260–267, Elsevier Science Inc. (1995).

Eikmanns, B.J., et al. "Cloning, Sequence Analysis, Expression, and Inactivation of the *Corynebacterium glutamicum* icd Gene Encoding Isocitrate Dehydrogenase and Biochemical Characterization of the Enzyme," *J. Bacteriol.* 177:774–782, American Society for Microbiology (1995).

Suye, S.–i., "Coenzyme regeneration with malic enzyme reaction system," in: *Recent Research Developments in Fermantation & Bio–engineering*, Vol. 1, Pandalai, S.G., ed. Research Signpost, Trivandrum, India, pp. 55–64 (Dec. 1998).

```
    ATGGCGGACATTTCGACCACCCAGGCTTGGCAAGACCTGACCGATCATTACTCAAACTTC
  1 ---------+---------+---------+---------+---------+---------+ 60
    M  A  D  I  S  T  T  Q  A  W  Q  D  L  T  D  H  Y  S  N  F

CAGGCAACCACTCTGCGTGAACTTTTCAAGGAAGAAAACCGCGCCGAGAAGTACACCTTC
 61 ---------+---------+---------+---------+---------+---------+ 120
    Q  A  T  T  L  R  E  L  F  K  E  E  N  R  A  E  K  Y  T  F

TCCGCGGCTGGCCTCCACGTCGACCTGTCGAAGAATCTGCTTGACGACGCCACCCTCACC
121 ---------+---------+---------+---------+---------+---------+ 180
    S  A  A  G  L  H  V  D  L  S  K  N  L  L  D  D  A  T  L  T

AAGCTCCTTGCACTGACCGAAGAATCTGGCCTTCGCGAACGCATTGACGCGATGTTTGCC
181 ---------+---------+---------+---------+---------+---------+ 240
    K  L  L  A  L  T  E  E  S  G  L  R  E  R  I  D  A  M  F  A

GGTGAACACCTCAACAACACCGAAGACCGCGCTGTCCTCCACACCGCGCTGCGCCTTCCT
241 ---------+---------+---------+---------+---------+---------+ 300
    G  E  H  L  N  N  T  E  D  R  A  V  L  H  T  A  L  R  L  P

CCCGAAGCTGATCTGTCAGTAGATGGCCAAGATGTTGCTGCTGATGTCCACGAAGTTTTG
301 ---------+---------+---------+---------+---------+---------+ 360
    P  E  A  D  L  S  V  D  G  Q  D  V  A  A  D  V  H  E  V  L

GGACGCATGCGTGACTTCGCTACTGCGCTGCGCTCAGGCAACTGGTTGGGACACACCGGC
361 ---------+---------+---------+---------+---------+---------+ 420
    G  R  M  R  D  F  A  T  A  L  R  S  G  N  W  L  G  H  T  G

CACACGATCAAGAAGATCGTCAACATTGGTATCGGTGGCTCTGACCTCGGACCAGCCATG
421 ---------+---------+---------+---------+---------+---------+ 480
    H  T  I  K  K  I  V  N  I  G  I  G  G  S  D  L  G  P  A  M

GCTACGAAGGCTCTGCGTGCATACGCGACCGCTGGTATCTCAGCAGAATTCGTCTCCAAC
481 ---------+---------+---------+---------+---------+---------+ 540
    A  T  K  A  L  R  A  Y  A  T  A  G  I  S  A  E  F  V  S  N

GTCGACCCAGCAGACCTCGTTTCTGTGTTGGAAGACCTCGATGCAGAATCCACATTGTTC
541 ---------+---------+---------+---------+---------+---------+ 600
    V  D  P  A  D  L  V  S  V  L  E  D  L  D  A  E  S  T  L  F
```

FIG.1A

```
     GTGATCGCTTCGAAAACTTTTACCACCCAGGAGACGCTGTCTAACGCTCGTGCAGCTCGT
601  ---------+---------+---------+---------+---------+---------+ 660
      V  I  A  S  K  T  F  T  T  Q  E  T  L  S  N  A  R  A  A  R

GCTTGGCTGGTAGAGAAGCTCGGTGAAGAGGCTGTCGCGAAGCATTTCGTCGCAGTGTCC
661  ---------+---------+---------+---------+---------+---------+ 720
      A  W  L  V  E  K  L  G  E  E  A  V  A  K  H  F  V  A  V  S

ACCAATGCTGAAAAGGTCGCAGAGTTCGGTATCGACACGGACAACATGTTCGGCTTCTGG
721  ---------+---------+---------+---------+---------+---------+ 780
      T  N  A  E  K  V  A  E  F  G  I  D  T  D  N  M  F  G  F  W

GACTGGGTCGGAGGTCGTTACTCCGTGGACTCCGCAGTTGGTCTTTCCCTCATGGCAGTG
781  ---------+---------+---------+---------+---------+---------+ 840
      D  W  V  G  G  R  Y  S  V  D  S  A  V  G  L  S  L  M  A  V

ATCGGCCCTCGCGACTTCATGCGTTTCCTCGGTGGATTCCACGCGATGGATGAACACTTC
841  ---------+---------+---------+---------+---------+---------+ 900
      I  G  P  R  D  F  M  R  F  L  G  G  F  H  A  M  D  E  H  F

CGCACCACCAAGTTCGAAGAGAACGTTCCAATCTTGATGGCTCTGCTCGGTGTCTGGTAC
901  ---------+---------+---------+---------+---------+---------+ 960
      R  T  T  K  F  E  E  N  V  P  I  L  M  A  L  L  G  V  W  Y

TCCGATTTCTATGGTGCAGAAACCCACGCTGTCCTACCTTATTCCGAGGATCTCAGCCGT
961  ---------+---------+---------+---------+---------+---------+ 1020
      S  D  F  Y  G  A  E  T  H  A  V  L  P  Y  S  E  D  L  S  R

TTTGCTGCTTACCTCCAGCAGCTGACCATGGAATCAAACGGCAAGTCAGTCCACCGCGAC
1021 ---------+---------+---------+---------+---------+---------+ 1080
      F  A  A  Y  L  Q  Q  L  T  M  E  S  N  G  K  S  V  H  R  D

GGCTCCCCTGTTTCCACTGGCACTGGCGAAATTTACTGGGGTGAGCCTGGCACAAATGGC
1081 ---------+---------+---------+---------+---------+---------+ 1140
      G  S  P  V  S  T  G  T  G  E  I  Y  W  G  E  P  G  T  N  G

CAGCACGCTTTCTTCCAGCTGATCCACCAGGGCACTCGCCTTGTTCCAGCTGATTTCATT
1141 ---------+---------+---------+---------+---------+---------+ 1200
      Q  H  A  F  F  Q  L  I  H  Q  G  T  R  L  V  P  A  D  F  I
```

FIG. 1B

```
      GGTTTCGCTCGTCCAAAGCAGGATCTTCCTGCCGGTGAGCGCACCATGCATGACCTTTTG
1201  ---------+---------+---------+---------+---------+---------+ 1260
      G  F  A  R  P  K  Q  D  L  P  A  G  E  R  T  M  H  D  L  L

ATGAGCAACTTCTTCGCACAGACCAAGGTTTTGGCTTTCGGTAAGAACGCTGAAGAGATC
1261  ---------+---------+---------+---------+---------+---------+ 1320
      M  S  N  F  F  A  Q  T  K  V  L  A  F  G  K  N  A  E  E  I

GCTGCGGAAGGTGTCGCACCTGAGCTGGTCAACCACAAGGTCATGCCAGGTAATCGCCCA
1321  ---------+---------+---------+---------+---------+---------+ 1380
      A  A  E  G  V  A  P  E  L  V  N  H  K  V  M  P  G  N  R  P

ACCACCACCATTTTGGCGGAGGAACTTACCCCTTCTATTCTCGGTGCGTTGATCGCTTTG
1381  ---------+---------+---------+---------+---------+---------+ 1440
      T  T  T  I  L  A  E  E  L  T  P  S  I  L  G  A  L  I  A  L

TACGAACACATCGTGATGGTTCAGGGCGTGATTTGGGACATCAACTCCTTCGACCAATGG
1441  ---------+---------+---------+---------+---------+---------+ 1500
      Y  E  H  I  V  M  V  Q  G  V  I  W  D  I  N  S  F  D  Q  W

GGTGTTGAACTGGGCAAACAGCAGGCAAATGACCTCGCTCCGGCTGTCTCTGGTGAAGAG
1501  ---------+---------+---------+---------+---------+---------+ 1560
      G  V  E  L  G  K  Q  Q  A  N  D  L  A  P  A  V  S  G  E  E

GATGTTGACTCGGGAGATTCTTCCACTGATTCACTGATTAAGTGGTACCGCGCAAATAGG
1561  ---------+---------+---------+---------+---------+---------+ 1620
      D  V  D  S  G  D  S  S  T  D  S  L  I  K  W  Y  R  A  N  R

TAG
1621  --- 1623
      *
```

FIG.1C

GENE ENCODING PHOSPHOGLUCOISOMERASE

CROSS-REFERENCE TO RELATED APPLICATIONS

This application claims the benefit of the following: U.S. Application No. 60/145,217, filed Jul. 23, 1999 and U.S. Application No. 60/150,017, filed Aug. 20, 1999, both of which contents are incorporated herein by reference.

BACKGROUND OF THE INVENTION

1. Field of the Invention

The present invention relates, in general, to a method of producing L-amino acids and to a gene encoding phosphoglucoisomerase.

2. Background Information

Bacterial cells are used industrially to produce amino acids by fermentation processes (Ishino, S. et al., *J. Gen. Appl. Microbiol.* 37:157–165 (1991), Kinoshita, S., Nakayama, K. and Nagasaki, S., *J. Gen. Appl. Microbiol.* 4:128–129 (1958)). Although numerous research reports and reviews have appeared concerning fermentation process and the mechanisms of accumulation of amino acids, more progress needs to be made to increase the yields of amino acids from microorganisms (Ishino, S. et al., *J. Gen. Appl. Micorobiol.* 37:157–165 (1991), Aida, K. et al., eds., "Biotechnology of Amino Acid Production," Kodansha (Tokyo)/Elsevier (New York) (1986) and Marx, A. et al., *Metabolic Engineering* 1:35–48 (1999)).

There has been some success in using metabolic engineering to direct the flux of glucose derived carbons toward aromatic amino acid formation (Flores, N. et al., *Nature Biotechnol.* 14:620–623 (1996)). However, the successful application in producer strains has not yet been documented (Berry, A., *TIBTECH* 14:250–256 (1996)).

Metabolic engineering relates to manipulation of the flow of carbons of starting materials, such as carbohydrates and organic acids, through the variety of metabolic pathways during fermentation. Studies have been done, for example, on the central metabolism of *Corynebacterium glutamicum* using $^{13}C$ NMR studies (Ishino, S. et al., *J. Gen. Appl. Microbiol.* 37:157–165 (1991), Marx, A. et al., *Biotechnology and Bioengineering* 49:111–129 (1996)). Additionally, also using $^{13}C$ NMR, Walker et al. (Walker, T. et al., *J. Biol. Chem.* 257:1189–1195 (1982)) analyzed glutamic acid fermentation by *Microbacterium ammoniaphilum,* and Inbar et al. (Inbar, L. et al., *Eur. J. Biochem.* 149:601–607 (1985)) studied lysine fermentation by *Brevibacterium flavum.*

The present invention solves a problem of improving yields of amino acids during fermentation using metabolic engineering.

SUMMARY OF THE INVENTION

The present invention provides a method of producing L-amino acids by culturing altered bacterial cells having increased amounts of NADPH as compared to unaltered bacterial cells, whereby L-amino acid yields from said altered bacterial cells are greater than yields from unaltered bacterial cells.

The present invention also provides a method of producing a bacterial cell with a mutated phosphoglucose isomerase (pgi) gene comprising (a) subcloning an internal region of the pgi gene into a suicide vector; and (b) inserting said suicide vector into a bacterial genome, via homologous recombination, whereby a bacterial cell with an altered pgi gene is produced. The invention further provides an altered bacterial cell produced according to this method.

The invention also provides a vector useful according to this method.

The present invention further provides isolated nucleic acid molecules comprising a polynucleotide encoding the *Corynebacterium glutamicum* phosphoglucose isomerase polypeptide having the amino acid sequence shown in FIG. 1 (SEQ ID NO:2) or one of the amino acid sequence encoded by the DNA clone deposited in a bacterial host as NRRL Deposit Number B-30174 on Aug. 17, 1999.

The present invention also relates to recombinant vectors, which include the isolated nucleic acid molecules of the present invention, and to host cells containing the recombinant vectors, as well as to methods of making such vectors and host cells and for using them for production of Pgi polypeptides or peptides by recombinant techniques.

The invention further provides an isolated Pgi peptide having an amino acid sequence encoded by a polynucleotide described herein.

Further advantages of the present invention will be clear from the description that follows.

BRIEF DESCRIPTION OF THE FIGURES

FIGS. 1A–1C shows the nucleotide (SEQ ID NO:1) and deduced amino acid (SEQ ID NO:2) sequences of pgi. The Pgi peptide has a deduced molecular weight of about 59 KDa.

DETAILED DESCRIPTION OF THE INVENTION

It has been determined herein that increased amounts of NADPH in a bacterial cell increase product yield, specifically in anabolic processes where NADPH is a limiting factor. A way of carrying chemical energy from reactions of catabolism to the energy-requiring reactions of biosynthesis, such as the formation of amino acids, is in the form of hydrogen atoms or electrons. To be effective as reducing agents, hydrogen atoms must have considerable free energy. Such high-energy hydrogen atoms are obtained from cell fuels by dehydrogenases, which catalyze removal of hydrogen atoms from fuel molecules and their transfer to specific coenzymes, particularly to the oxidized form of nicotinamide adenine dinucleotide phosphate ($NADP^+$). The reduced, or hydrogen-carrying, form of this coenzyme, designated NADPH, is a carrier of energy-rich electrons from catabolic reactions to electron-requiring biosynthetic reactions.

The present invention provides a method for producing L-amino acids by culturing altered bacterial cells having increased amounts of NADPH as compared to unaltered bacterial cells whereby L-amino acid yields from said altered bacterial cells are greater than yields from unaltered bacterial cells. Preferred amino acids are L-lysine, L-threonine and L-isoleucine. As used herein, an altered bacterial cell is defined as a bacterial cell which has increased amount of NADPH as compared to an unaltered bacterial cell.

In one preferred embodiment, an "altered" bacterial cell is a "mutated" bacterial cell. A "mutation" is any detectable change in the genetic material which can be transmitted to daughter cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens or recombinant DNA technology. A mutant variation of a nucleic acid molecule results from a mutation. A mutant polypeptide can result from a mutant nucleic acid molecule.

Additionally, an altered or mutated bacterial cell can be genetically "mutated" to yield an increased amount of NADPH as compared to the genetically "unmutated" cell.

An increased amount of NADPH in the altered bacterial cell results in increased production of amino acids. Preferably, in an altered bacterial cell, amino acid yields are increased over yields from the unaltered cell from greater than about 1%, and preferably from about 1% to about 100%, preferably from about 2% to about 80%, and more preferably, from about 5% to about 60%, and even more preferably from about 10% to about 80%. As used herein, "yield" is defined as grams of amino acid produced, multiplied by 100, divided by grams of glucose consumed.

In agreement with the present invention, the altered bacterial cell of the present invention is cultured in a culture medium that comprises a carbon source and a nitrogen source. The carbon source can be, for example, arabinose, cellobiose, fructose, glucose, lactose, maltose, mannose, rhamnose, raffinose, sorbose, sucrose, trehalose, pyruvate, or succinate. The carbon source is preferably at an initial concentration of 0.1 to 10%, preferably 0.5 to 6.0% by weight. All of the carbon source can be added to the medium before the start of culturing, or it can be added step by step or continuously during culturing.

The medium used herein can be solid or liquid, synthetic (i.e. man-made) or natural, and contains sufficient nutrients for the cultivation of the altered bacterial cell of the present invention. Preferably, the medium employed is a liquid medium, more preferably a synthetic liquid medium.

The natural or synthetic culture media used in the above and below described embodiments of the invention also contain a nitrogen source, suitable inorganic salts, and, as appropriate, various trace nutrients, growth factors and the like suitable for cultivation of the altered bacterial cell, and can also contain at least one supplementary carbon source. The amount of each of these additional ingredients to be employed is preferably selected to maximize amino acid production. Such amounts can be determined empirically by one skilled in the art according to the various methods and techniques known in the art.

Illustrative examples of suitable supplemental carbon sources include, but are not limited to: other carbohydrates, such as glucose, fructose, sucrose, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts include, but are not limited to: salts of potassium, calcium, sodium, magnesium, manganese, iron, cobalt, zinc, copper, molybdenum, tungsten and other trace elements, and phosphoric acid.

Illustrative examples of appropriate trace nutrients, growth factors, and the like include, but are not limited to: coenzyme A, pantothenic acid, pyridoxine-HCl, biotin, thiamine, riboflavin, flavine mononucleotide, flavine adenine dinucleotide, DL-6,8-thioctic acid, folic acid, Vitamin $B_{12}$, other vitamins, bases such as adenine, uracil, guanine, thymine and cytosine, L amino acids, sodium thiosulfate, p- or r-aminobenzoic acid, niacinamide, nitriloacetate, and the like, either as pure or partially purified chemical compounds or as present in natural materials. Cultivation of the inventive microorganism strain can be accomplished using any of the submerged fermentation techniques known to those skilled in the art, such as airlift, traditional sparged-agitated designs, or in shaking culture.

The culture conditions employed, including temperature, pH, aeration rate, agitation rate, culture duration, and the like, can be determined empirically by one skilled in the art to maximize amino acid production. The selection of specific culture conditions depends upon factors such as medium composition and type, culture technique, and similar considerations.

After cultivation for a sufficient period of time, until one or more kinds of amino acids that have accumulated in the cells and/or culture broth can be isolated according to any of the known methods including ion exchange chromatography, gel filtration, solvent extraction, affinity chromatography, or any combination thereof. Any method that is suitable with the conditions employed for cultivation can be used.

Preferred bacterial cells are Corynebacterial species and *Escherichia coli*. Preferred among bacterial cells are *Corynebacterium glutamicum* cells. As used herein, *Brevibacterium flavum* and *Brevibacterium lactofermentum* are synonymous with *Corynebacterium glutamicum*.

In the present invention, in general, increased NADPH within a microorganism is achieved by altering the carbon flux distribution between the glycolytic and pentose phosphate pathways of that organism. As used herein, "carbon flux" refers to the number of glucose molecules which proceed down a particular metabolic path relative to competing paths.

Preferably, NADPH availability is increased by increasing the carbon flux through the oxidative branch of the pentose phosphate pathway. Theoretically, 12 NADPH's are generated per glucose when glucose is exclusively metabolized in the pentose phosphate pathway, but only two NADPH's are produced per glucose metabolized in the TCA cycle (tricarboxylic acid, also called the citric acid cycle). Ishino, S. et al., *J. Gen. Appl. Microbiol* 37:157–165 (1991). The present invention provides a method of producing L-amino acids by culturing an altered bacterial cell which has an increase in the carbon flux through the pentose phosphate pathway.

Most of the glucose catabolized in living organisms proceeds through glycolysis resulting in the formation of pyruvate. The pentose phosphate pathway, also called the hexose monophosphate shunt, is an alternative route for glucose catabolism. The pentose phosphate pathway produces NADPH and under lysine fermentation conditions is more active. Ishino, S. et al., *J. Gen. Appl. Microbiol.* 37:157–165 (1991).

In the present invention, an altered bacterial cell can be one in which carbon flux though the oxidative branch of the pentose phosphate pathway is increased. Specifically, in the present invention, an altered bacterial cell can be one which has an increased amount of one or more enzymes involved in the pentose phosphate pathway. Such pentose phosphate enzymes are selected from the group comprising glucose 6-phosphate dehydrogenase, transketolase, transaldolase, ribulose 5-phosphate-3-epimerase, ribulose 5-phosphate isomerase and 6-phosphogluconate dehydrogenase, and 6-phosphogluconolactonase.

In a preferred embodiment, the present invention further provides a method of producing L-amino acids by culturing an altered bacterial cell with an increased amount of malic enzyme relative to an unaltered cell. Malic enzyme catalyzes the reaction of malate with $NADP^+$ to produce pyruvate, carbon dioxide, NADPH and $H^+$.

In a preferred embodiment, the present invention further provides a method of producing L-amino acids by culturing an altered bacterial cell with an increased amount of isocitrate dehydrogenase relative to an unaltered cell. Isocitrate dehydrogenase catalyzes the reaction of isocitrate with $NADP^+$ to produce α-ketoglutarate, carbon dioxide, NADPH and $H^+$.

Both glycolysis and the pentose phosphate pathway compete for glucose. In the present invention, an altered bacterial cell can be one in which a decrease or blockage of the carbon flux though glycolysis results in an increase in the carbon flux though the oxidative branch of the pentose phosphate pathway. As used in the present invention, an altered bacterial cell can be one in which a decrease in carbon flux through glycolysis is achieved through decreasing the amount of one or more enzyme(s) involved in glycolysis. Preferred enzymes are 6-phosphoglucose isomerase, fructose diphosphate aldolase, D-glyceraldehyde phosphate dehydrogenase, phosphoglycerate kinase, phosphoglycerate mutase, endolase or pyruvate kinase. A preferred enzyme is 6-phosphoglucose isomerase.

A preferred method of decreasing the amount of a glycolytic enzyme in an altered bacterial cell is by mutating the gene which encodes the enzyme. As used herein, preferred is blocking (null) or weakening (decreased) expression of the gene encoding 6-phosphoglucose isomerase ("pgi").

A preferred method of blocking (null) or weakening (decreased) expression of genes encoding enzymes involved in glycolysis is by using suicide vectors (also called integrative vectors). As used herein, a suicide vector is defined as a vector which does not replicate autonomously within a particular organism, which then is introduced into the cell and recombines into a homologous region of the organism's chromosome to cause insertional inactivation of the homologous gene. Insertional inactivation of the gene is achieved by disrupting the reading frame of the gene. Insertional inactivation of the gene occurs only if an internal portion of the gene is used as the homologous region.

Recombinant constructs can be introduced into the bacterial cells of the present invention using well known techniques such as transduction, transfection, transvection, conjugation, electroporation, electrotransformation, calcium phosphate transfection, DEAE-dextran mediated transfection, cationic lipid-mediated transfection, and transformation or other methods. Such methods are described in many standard laboratory manuals, such as Davis et al., "Basic Methods in Molecular Biology," (1986).

In a preferred embodiment, the altered bacterial cell is produced by (a) subcloning an internal region of the pgi gene into a suicide vector; and (b) inserting said suicide vector into a bacterial genome via homologous recombination. An internal region can be defined as a contiguous DNA sequence between but not including the initiation codon and final codon of the open reading frame (ORF) in question. Preferably an internal region is chosen which will facilitate genomic integration and result in the expression of a non-functional polypeptide from the ORF in question.

In certain preferred embodiments, the suicide vectors can be inducible, mutant-specific and/or condition-specific. Particularly preferred among such vectors are those inducible by environmental factors that are easy to manipulate, such as temperature and nutrient additives. Other suitable environmental factors will be readily apparent to the skilled artisan.

The altered bacterial cells of the present invention can be transformed with suicide vectors which optionally include at least one marker gene. Such markers include amikacin, augmentin (amoxicillin plus clavulonic acid), ampicillin, cefazolin, cefoxitin, ceftazidime, ceftiofur, cephalothin, chloramphenicol, enrofloxacin, erythromycin, florfenicol, gentamicin, imipenem, kanamycin, sarafloxicin, tetracycline, ticarcillin, streptomycin, spectinomycin, hygromycin, trimethoprim or tilmicosin resistance genes. Preferred markers include chloramphenicol and/or kanamycin resistance genes. Other suitable markers will be readily apparent to the skilled artisan.

An illustrative example of the use of suicide vectors is as follows: an internal region of a gene is amplified via the polymerase chain reaction, and the fragment resulting from the amplification is subcloned into a suicide vector which includes an antibiotic resistance marker gene, and the suicide vector is transformed into the original organism. The recovery of antibiotic resistant clones implies insertional inactivation of the homologous gene. The suicide vector used can include any plasmid incapable of autonomous replication in the target organism. In cases where the target organism is not *Escherichia coli,* Col E1 based replicons are preferred. Among Col E1 based replicons pBGS131 (American Type Culture Collection (ATCC), Manassas, Va., Deposit No. 37443) is preferred.

In a preferred embodiment, the present invention further provides a method of producing a bacterial cell with a mutated pgi gene. In a particularly preferred embodiment, the invention provides a method of producing a bacterial cell with a mutated pgi gene comprising (a) subcloning an internal region of the pgi gene into a suicide vector; and (b) inserting said suicide vector into a bacterial genome via homologous recombination whereby a bacterial cell with an altered pgi gene is produced.

In a further embodiment, the present invention provides a bacterial cell produced according to the above-described methods.

An illustrative example of production of an altered bacterial cell follows. A region of the *Corynebacterium glutamicum* (*C. glutamicum*) pgi gene which encodes 6-phosphoglucose isomerase (a glycolytic enzyme), is amplified by PCR using suitable primers. Preferably, the PCR primers are those listed in SEQ ID NO:3 and SEQ ID NO:4, which contain the recognition sequence for the restriction enzyme Hind III. Following restriction with Hind III, the PCR product, is then subcloned into the suicide vector pBGS131. The resulting subclone is designated pDPTpgi2. The subclone pDPTpgi2 is then transformed into *C. glutamicum* and kanamycin resistant colonies are selected for on appropriate media. The isolation of kanamycin resistant colonies implies that an integration event has occurred.

Predominantly the integration occurs via homologous recombination resulting in disruption of the pgi gene.

Another preferred method of producing an altered bacterial cell is by blocking or weakening expression of the appropriate gene through alteration of the promoter in front of the gene. Preferred is by using a different promoter from any source or changing the nucleotide sequence of the native promoter. Preferred among methods of changing the nucleotide sequence of the native promoter is PCR mutagenesis. Among known bacterial promoters suitable for this use in the present invention include the *E. coli* lacI and lacZ promoters, the T3 and T7 promoters, the gpt promoter, the lambda $P_R$ and $P_L$ promoters, the trp promoter, the tac promoter or promoters endogenous to the bacterial cells of the present invention. Also preferred is upregulation of genes encoding enzymes involved in the pentose phosphate pathway. This can be done by alteration of the promoter controlling the gene such that a stronger promoter than the native promoter is used. Another preferred way of upregulating the genes of the pentose phosphate pathway would be increasing the copy number of the genes in question through the use of genomic integration or autonomously replicating plasmids.

In a preferred embodiment, the present invention also provides a method of producing L-amino acids comprising culturing an altered bacterial cell, wherein said bacterial cell is a *Corynebacterium glutamicum* cell with a gene selected from the group consisting of a mutant pgi gene.

Another preferred method of producing an altered bacterial cell comprises mutating a gene which encodes an enzyme involved in glycolysis to produce blocked or weakened expression of the gene encoding the glycolytic enzyme. Illustrative examples of suitable methods for preparing mutated genes include, but are not limited to: PCR mutagenesis, in vitro chemical mutagenesis, oligonucleotide mutagenesis, mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by insertional elements or transposons or by homologous recombination of transforming linear or circular DNA molecules; and transduction mediated by bacteriophages such as P1. These methods are well known in the art and are described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla.(1995); *Methods in Plant Molecular Biology and Biotechnology,* B. R. Glick and J. E. Thompson, eds., CRC Press, Boca Raton, Fla. (1993); and P. F. Smith-Keary, *Molecular Genetics of Escherichia coli,* The Guilford Press, New York, N.Y. (1989).

In a preferred embodiment, the present invention further provides an isolated or purified bacterial cell comprising a mutated pgi gene.

The present invention further provides isolated nucleic acid molecules comprising a polynucleotide encoding a Pgi polypeptide having the amino acid sequence shown in FIG. 1 (SEQ ID NO:2). The nucleotide sequence shown in FIG. 1 (SEQ ID NO:1) can be obtained by sequencing the DNA clone, which was deposited on Aug. 17, 1999 at the Agricultural Research Service Culture Collection (NRRL) under the terms of the Budapest Treaty, 1815 North University Street, Peoria, Ill. 61604, USA and given accession number B-30174. The deposited clone is in the p41-13(C01) plasmid.

The present invention provides an isolated nucleic acid molecule selected from the group consisting of:
 (a) a polynucleotide encoding a polypeptide comprising amino acids from about 1 to about 540 in SEQ ID NO:2;
 (b) a polynucleotide encoding a polypeptide comprising one of the amino acid sequences encoded by the DNA clone contained in NRRL Deposit No. B-30174;
 (c) the complement of (a) or (b);
 (d) a polynucleotide variant created by altering the polynucleotide of (a), wherein:
  (1) said altering includes a nucleotide insertion, deletion, or substitution, or any combination thereof; and
  (2) the number of alterations is equal to or less than 5% of the total number of nucleotides present in (a);
 (e) a polynucleotide variant created by altering the polynucleotide of (b), wherein:
  (1) said altering includes a nucleotide insertion, deletion, or substitution, or any combination thereof; and
  (2) the number of alterations is equal to or less than 5% of the total number of nucleotides present in (b);
 (f) a polynucleotide variant created by altering the polynucleotide of (c), wherein:
  (1) said altering includes a nucleotide insertion, deletion, or substitution, or any combination thereof, and
  (2) the number of alterations is equal to or less than 5% of the total number of nucleotides present in (c).

The present invention further provides the above nucleic acid molecule wherein said polynucleotide has the complete nucleotide sequence in SEQ ID NO:1.

The present invention further provides the above nucleic acid molecule wherein said polynucleotide has the nucleotide sequence in SEQ ID NO:1 encoding the Pgi polypeptide having the complete amino acid sequence in SEQ ID NO:2.

The present invention further provides the above nucleic acid molecule wherein said polynucleotide has a nucleotide sequence encoding the Pgi polypeptide encoded by a DNA clone contained in NRRL Deposit No. B-30174.

The present invention further provides an isolated nucleic acid molecule comprising a polynucleotide which hybridizes under stringent hybridization conditions to a polynucleotide having a nucleotide sequence identical to a nucleotide sequence in (a), (b), or (c) of the above nucleic acid molecule, wherein said polynucleotide which hybridizes does not hybridize under stringent hybridization conditions to a polynucleotide having a nucleotide sequence consisting of only A residues or of only T residues.

The present invention further provides a method for making a recombinant vector comprising inserting the above isolated nucleic acid molecule into a vector.

The present invention further provides a vector comprising the above nucleic acid molecule. The present invention further provides a method of making a recombinant host cell comprising introducing the above vector into a host cell. The present invention further provides a host cell comprising the above vector. The present invention further provides a method for producing a Pgi polypeptide, comprising culturing the above recombinant host cell under conditions such that said polypeptide is expressed and recovering said polypeptide.

The present invention further provides an isolated polypeptide selected from the group consisting of:
  (a) a polypeptide comprising amino acids from about 1 to about 540 in SEQ ID NO:2;
  (b) a polypeptide comprising the amino acid sequence encoded by the DNA clone contained in NRRL Deposit No. B-30174;
  (c) a polypeptide variant created by altering the amino acid sequence of (a), wherein:
    (1) said altering includes an insertion, deletion, or substitution, or any combination thereof; and
    (2) the number of alterations is equal to or less than 5% of the total number of amino acids present in (a);
  (d) a polypeptide variant created by altering the polynucleotide of (b), wherein:
    (1) said altering includes an insertion, deletion, or substitution, or any combination thereof; and
    (2) the number of alterations is equal to or less than 5% of the total number of amino acids present in (b).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1, a nucleic acid molecule of the present invention encoding a Pgi polypeptide may be obtained using standard cloning and screening procedures.

Thus, the present invention provides a nucleotide sequence encoding the Pgi polypeptide having the amino acid sequence encoded by the clone contained in the host identified as NRRL Deposit No. B-30174 and as shown in FIG. 1 (SEQ ID NOs:1 and 2).

As one of ordinary skill would appreciate, due to the possibilities of sequencing errors, the predicted Pgi polypeptide encoded by the deposited clone comprise about 540 amino acids, but may be anywhere in the range of 500 to 580 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIG. 1 (SEQ ID NO:1); DNA molecules comprising the coding sequence for the Pgi protein shown in FIG. 1 (SEQ ID NO:2); and DNA molecules which comprise a sequence substantially different from those described above but which, due to the degeneracy of the genetic code, still encode the Pgi protein. Of course the genetic code is well known in the art. Thus, it would be routine for one skilled in the art to generate such degenerate variants.

In addition, the invention provides nucleic acid molecules having nucleotide sequences related to extensive portions of SEQ ID NO:1.

In another aspect, the invention provides isolated nucleic acid molecules encoding the Pgi polypeptide having an amino acid sequence encoded by the nucleic acid molecule deposited as NRRL Deposit No. B-30174 on Aug. 17, 1999. The invention further provides an isolated nucleic acid molecule having the nucleotide sequence shown in FIG. 1 (SEQ ID NO:1) or the nucleotide sequence of the pgi genomic sequence contained in the above-described deposited clone, or a nucleic acid molecule having a sequence complementary to one of the above sequences. Such isolated molecules, particularly DNA molecules, are useful as probes for gene mapping, by in situ hybridization with chromosomes.

The present invention is further directed to fragments of the isolated nucleic acid molecules described herein. By a fragment of an isolated nucleic acid molecule having the nucleotide sequence of the deposited clone or the nucleotide sequence shown in FIG. 1 (SEQ ID NOs:1) is intended fragments at least about 15 nucleotides (nt), and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 300, 325, 350, 375, 400, 425, 450, 475, 500, 525, 550 nt in length are also useful according to the present invention as are fragments corresponding to most, if not all, of the nucleotide sequence of the deposited clone or as shown in FIG. 1 (SEQ ID NOs:1). By a fragment at least 20 nt in length, for example, is intended fragments which include 20 or more contiguous bases from the nucleotide sequence of the deposited clone or the nucleotide sequence as shown in FIG. 1 (SEQ ID NO:1).

In another aspect, the invention provides an isolated nucleic acid molecule comprising a polynucleotide which hybridizes under stringent hybridization conditions to a portion of the polynucleotide in a nucleic acid molecule of the invention described above, for instance, the deposited clone contained in NRRL Deposit B-30174. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited clone or the nucleotide sequence as shown in FIG. 1 (SEQ ID NO:1). Of course, a polynucleotide which hybridizes only to a polyA sequence (such as the 3' terminal poly(A) tract of the pgi cDNA shown in FIG. 1 (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a Pgi polypeptide may include, but are not limited to those encoding the amino acid sequence of the polypeptide, by itself, the coding sequence for the polypeptide and additional sequences, such as those encoding an amino acid leader or secretory sequence, such as a pre-, or pro- or prepro-protein sequence; the coding sequence of the polypeptide, with or without the aforementioned additional coding sequences, together with additional, non-coding sequences, including for example, but not limited to non-coding 5' and 3' sequences, such as the transcribed, non-translated sequences that play a role in transcription, mRNA processing, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the Pgi fused to Fc at the − or C-terminus.

The probes, primers, and/or nucleic acid fragments described above can be used to monitor expression of the pgi gene during fermentation.

The present invention further relates to variants of the nucleic acid molecules of the present invention, which encode portions, analogs or derivatives of the Pgi protein. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Pgi protein or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to (a) a nucleotide sequence encoding the polypeptide having the amino acid sequence in SEQ ID NO:2; (b) a nucleotide sequence encoding the full-length Pgi polypeptide having the complete amino acid sequence encoded by the clone contained in NRRL Deposit No. B-30174; or (c) a nucleotide sequence complementary to any of the nucleotide sequences in (a) or (b).

By a polynucleotide having a nucleotide sequence at least, for example, 95% "identical" to a reference nucleotide sequence encoding a Pgi polypeptide is intended that the nucleotide sequence of the polynucleotide is identical to the reference sequence except that the polynucleotide sequence may include up to five point mutations per each 100 nucleotides of the reference nucleotide sequence encoding the Pgi polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in FIG. 1 or to the nucleotides sequence of the deposited clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in FIG. 1 (SEQ ID NO:1) or to the nucleic acid sequence of the deposited clone, irrespective of whether they encode a polypeptide having Pgi activity. This is because even where a particular nucleic acid molecule does not encode a polypeptide having Pgi activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Pgi activity include, inter alia, isolating the pgi gene or allelic variants thereof in a genomic library and Northern Blot analysis for detecting pgi mRNA expression.

Preferred, however, are nucleic acid molecules having sequences at least 95%, 96%, 97%, 98% or 99% identical to the nucleic acid sequence shown in FIG. 1 (SEQ ID NO:1) or to the nucleic acid sequence of the deposited clone which do, in fact, encode a polypeptide having Pgi protein activity. By "a polypeptide having Pgi activity" is intended polypeptides exhibiting activity similar, but not necessarily identical, to an activity of the Pgi protein of the invention, as measured in a particular biological assay.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited clone or the nucleic acid sequence shown in FIG. 1 (SEQ ID NO:1) will encode a polypeptide "having Pgi protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Pgi protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," I:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of Pgi polypeptides or fragments thereof by recombinant techniques.

The polynucleotides may be joined to a vector containing a selectable marker for propagation in a host. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include but are not limited to kanamycin chloramphenicol, tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells. Appropriate culture mediums and conditions for the above-described host cells are known in the art.

Among known bacterial promoters suitable for use in the production of proteins of the present invention include the E. coli lacI and lacZ promoters, the T3 and T7 promoters, the gpt promoter, the lambda PR and PL promoters and the trp promoter.

Thus, the present invention is also directed to expression vector useful for the production of the proteins of the present invention.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

The Pgi protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Pgi Polypeptides and Fragments

The invention further provides an isolated Pgi polypeptide having the amino acid sequence encoded by the deposited clone, or the amino acid sequence in FIG. 1 (SEQ ID NO:2), or a peptide or polypeptide comprising a portion of the above polypeptides.

It will be recognized in the art that some amino acid sequences of the Pgi polypeptide can be varied without significant effect of the structure or function of the protein. If such differences in sequence are contemplated, it should be remembered that there will be critical areas on the protein which determine activity.

Thus, the invention farther includes variations of the Pgi polypeptide which show substantial Pgi polypeptide activity or which include regions of Pgi protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of FIG. 1 (SEQ ID NO:2), or the Pgi polypeptide encoded by the deposited clone, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of amino acid substitutions for any given Pgi polypeptide will not be more than 50, 40, 30, 20, 10, 5, or 3.

Amino acids in the Pgi protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for phosphoglucose isomerase activity.

The polypeptides of the present invention are preferably provided in an isolated form, and preferably are substantially purified. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the Pgi polypeptide can be substantially purified by the one-step method described in Smith and Johnson, *Gene* 67:31–40 (1988).

The polypeptides of the present invention include the Pgi polypeptide encoded by the deposited DNA and polypeptides which are at least 95% identical, still more preferably at least 96%, 97%, 98% or 99% identical to the polypeptides encoded by the deposited clone, to the polypeptide of FIG. 1 (SEQ ID NO:2), and also include portions of such polypeptides with at least 30 amino acids and more preferably at least 50 amino acids.

By a polypeptide having an amino acid sequence at least, for example, 95% "identical" to a reference amino acid sequence of a Pgi polypeptide is intended that the amino acid sequence of the polypeptide is identical to the reference sequence except that the polypeptide sequence may include up to five amino acid alterations per each 100 amino acids of the reference amino acid of the Pgi polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIG. 1 (SEQ ID NO:2) or to the amino acid sequence encoded by deposited clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

N-terminal and C-terminal Deletion Mutants

In one embodiment, the present invention provides polypeptides having one or more residues deleted from the amino terminus of the amino acid sequence of the Pgi polypeptide depicted in FIG. 1 or encoded by the DNA of the deposited clone. Particularly, in one embodiment, N-terminal deletions of the Pgi polypeptide can be described by the general formula m to 540, where m is any one of the integers from 2 to 539 corresponding to the position of the amino acid residue identified in SEQ ID NO:2 and, preferably, corresponds to one of the N-terminal amino acid residues identified in the N-terminal deletions specified herein. Polynucleotides encoding these polypeptides are also encompassed by the invention.

Further embodiments of the invention are directed to C-terminal deletions of the Pgi polypeptides of the invention, described by the general formula 1 to n, where n is any one of the integers from 2 to 539 corresponding to the position of amino acid residue identified in SEQ ID NO:2, and preferably corresponds to a residue identified in one of the C-terminal deletions specified herein. Polynucleotides encoding these polypeptides are also encompassed by the invention.

Further embodiments of the invention are directed to polypeptide fragments comprising, or alternatively, consisting of, amino acid residues described by the general formula m to n, where m and n correspond to any one of the amino acid residues specified above for these symbols, respectively. Polynucleotides encoding these polypeptides are also encompassed by the invention.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

EXAMPLES

Example 1

DNA Isolation and Purification

DNA was isolated from cultures of NRRL B-11474 cells. NRRL B-11474 cells were harvested from CM media (Table B) and suspended in 10 ml of TE pH 8 (10 mM Tris*Cl, 1 mM EDTA). Forty micrograms of RNase A and 10 milligrams of lysozyme were added per milliliter of suspension and the suspension was incubated at 37° C. for 30 minutes. The suspension was made 1.0% in sodium dodecyl sulfate (SDS) and 0.1 mg/l proteinase K was added, and the cells were lysed by incubation at 37° C. for 10 minutes. Nucleic acids were purified by three extractions with TE-saturated phenol (pH 7), followed by ethanol precipitation. Nucleic acid precipitates were twice washed with 80% ethanol and redissolved in TE pH 8. The concentrations of DNA were quantified spectrophotometrically at 260 nm. Purity of DNA preparations were determined spectrophotometrically (A260/A280 and A260/A230 ratios) and by agarose gel electrophoresis (0.8% agarose in 1×TAE).

Sequencing of genomic DNA was performed, as is known by one of ordinary skill in the art, by creating libraries of plasmids and cosmids using pGEM3 and Lorist 6, respectively. The C. glutamicum pgi gene was identified by homology to glucose-6-phosphate isomerase of Mycobacterium tuberculosis (Swiss Prot Accession number P77895, Swiss Prot ID G6PI_MYCTU).

Example 2

Increasing NADPH Availability by Disrupting Pgi

An increase in carbon flux through the oxidative branch of the pentose phosphate pathway was achieved by disrupting the pgi gene which encodes 6-phosphoglucose isomerase. Two PCR primers were designed from the genomic DNA sequence described above to facilitate the amplification of a 680 bp internal region of the C. glutamicum pgi gene. These primers were:

pgif* (SEQ ID NO:3) 5' gctgatgtccacgaagctttgggac 3'
pgir* (SEQ ID NO:4) 3' gctgagaaccttggaataaggtagg 3'

Primers pgif* and pgir* contain the recognition sequence for the restriction enzyme Hind III. In the case of pgir*, it was necessary to make three changes from the C. glutamicum nucleotide sequence to incorporate the Hind III recognition sequence. These Hind III restriction sites facilitated subcloning.

PCR amplification conditions were employed as follows. The final volume of each PCR reaction was 100 μl. 100 ng of each primer was used along with 50 ng of high molecular weight C. glutamicum ATCC 21799 genomic DNA and 2.5 units of Taq DNA polymerase. Reaction buffer was included at a concentration recommended by the manufacturer (Stratagene) and dNTPs were also included at a final concentration of 200 μM. Cycling parameters were as follows: 94° C. for 1 minute, followed by 94° C. for 30 seconds, 60° C. for 30 seconds and 72° C. for 1 minute (30 cycles), 72° C. for 7 minutes followed by refrigeration.

On restriction with Hind III, the PCR product was reduced in size to approximately 660 bp. This fragment was then subcloned into the suicide vector pBGS131. The resulting subclone was designated pDPTpgi2.

Following electrotransformation into competent C. glutamicum (NRRL B11474) cells, integrants were selected for on CM (Table B) agar plates containing kanamycin at a final concentration of 10 μg/ml. Enzyme assay confirmed the absence of phosphoglucose isomerase activity in the mutant strains, indicating that the pgi gene in these strains had been disrupted.

Shake flask experiments indicate that the C glutamicum (NRRL B11474) pgi mutants have improved lysine titers and yields when compared to C. glutamicum (NRRL B11474) (Table A).

TABLE A

| Lysine production on FM3 (Table C) media | | | |
| --- | --- | --- | --- |
| Strain | Growth | Titer | Yield |
| NRRL B11474 | 46 | 25 | 42 |
| NRRL B11474::pgi2A | 40 | 31 | 52 |

Growth = optical density at 660 nm
Titer = grams of lysine/liter of medium
Yield = (grams of lysine/grams of glucose consumed) * 100

TABLE B

| CM Media | | | |
|---|---|---|---|
| Volume: | 1000 ml | % Agar: | 0 |
| Sucrose | | 50 g | |
| KH2 PO4 | | 0.5 g | |
| K2 HPO4 | | 1.5 g | |
| Urea | | 3 g | |
| MgSO4*7H20 | | 0.5 g | |
| Polypeptone | | 20 g | |
| Beef Extract | | 5 g | |
| Biotin | | 12.5 ml (60 mg/L) | |
| Thiamine | | 25 ml (120 mg/L) | |
| Niacinamide | | 25 ml (5 g/L) | |
| L-Methionine | | 0.5 g | |
| L-Threonine | | 0.25 g | |
| L-Alanine | | 0.5 g | |
| Bring to volume | | 1000 mls with DI water. | |
| pH | | about 7.1 | |

TABLE C

| FM3 Media | |
|---|---|
| Per liter | |
| $(NH_4)_2SO_4$ | 50 g |
| $KH_2PO_4$ | 1 g |
| $MgSO_4*7H_2O$ | 0.4 g |
| $MnSO_4*H_2O$ | 0.01 g |
| $FeSO_4*7H_2O$ | 0.01 g |
| Biotin | 0.03 mg |
| Corn Steep Liquor | 4% dry solids final concentration |
| Glucose | 6% final concentration |
| $CaCO_3$ | 50 g |

Example 3

Disrupting the Gene Encoding 6-Phosphofructokinase (pfkA)

The gene encoding for 6-phosphofructokinase (pfkA) was disrupted in a method similar to that described for the pgi gene in Example 2. Disruption of the pfkA gene was verified by enzyme assay of extracts of the mutants and showed that 6-phosphofructokinase activity was lacking. Unexpectedly, the *C. glutamicum* (NRRL B-11474) pfkA mutants were unable to utilize glucose.

All patents and publications referred to herein are hereby expressly incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated nucleic acid molecule selected from the group consisting of:
   (a) a polynucleotide encoding a polypeptide comprising amino acids from about 1 to about 540 in SEQ ID NO:2;
   (b) a polynucleotide encoding the polypeptide encoded by the DNA clone contained in NRRL Deposit No. B-30174;
   (c) the complement of (a) or (b);
   (d) a polynucleotide variant created by altering the polynucleotide of (a), wherein:
      (1) said altering includes a nucleotide insertion, deletion, or substitution, or any combination thereof; and
      (2) the number of alterations is equal to or less than 5% of the total number of nucleotides present in (a);
   (e) a polynucleotide variant created by altering the polynucleotide of (b), wherein:
      (1) said altering includes a nucleotide insertion, deletion, or substitution, or any combination thereof; and
      (2) the number of alterations is equal to or less than 5% of the total number of nucleotides present in (b); and
   (f) a polynucleotide variant created by altering the polynucleotide of (c), wherein:
      (1) said altering includes a nucleotide insertion, deletion, or substitution, or any combination thereof; and
      (2) the number of alterations is equal to or less than 5% of the total number of nucleotides present in (c).

2. The nucleic acid molecule of claim 1, wherein said polynucleotide has the complete nucleotide sequence in SEQ ID NO:1.

3. The nucleic acid molecule of claim 1, wherein said polynucleotide has the nucleotide sequence in SEQ ID NO:1 encoding the phosphoglucoisomerase (Pgi) polypeptide having the complete amino acid sequence in SEQ ID NO:2.

4. The nucleic acid molecule of claim 1, wherein said polynucleotide has a nucleotide sequence encoding the Pgi polypeptide encoded by the DNA clone contained in NRRL Deposit No. B-30174.

5. An isolated nucleic acid molecule comprising a polynucleotide which hybridizes under stringent hybridization conditions to a polynucleotide having a nucleotide sequence identical to a nucleotide sequence in (a), (b), or (c) of claim 1, wherein said polynucleotide which hybridizes does not hybridize under stringent hybridization conditions to a polynucleotide having a nucleotide sequence consisting of only A residues or of only T residues.

6. A method for making a recombinant vector comprising inserting an isolated nucleic acid molecule of claim 1 into a vector.

7. A vector comprising the nucleic acid molecule of claim 1.

8. A method of making a recombinant host cell comprising introducing the vector of claim 7 into a host cell.

9. A host cell comprising the vector of claim 7.

10. A method for producing a Pgi polypeptide, comprising culturing the recombinant host cell of claim 9 under conditions such that said polypeptide is expressed and recovering said polypeptide.

* * * * *

SEQUENCE LISTING

```
<160> NUMBER OF SEQ ID NOS:  4

<210> SEQ ID NO 1
<211> LENGTH: 1623
<212> TYPE: DNA
<213> ORGANISM: Corynebacterium glutamicum
<220> FEATURE:
<221> NAME/KEY: CDS
<222> LOCATION: (1)..(1620)

<400> SEQUENCE: 1 atg gcg gac att tcg acc acc cag gct tgg caa gac ctg acc gat cat      48
Met Ala Asp Ile Ser Thr Thr Gln Ala Trp Gln Asp Leu Thr Asp His
  1               5                  10                  15 tac tca aac ttc cag gca acc act ctg cgt gaa ctt ttc aag gaa gaa      96
Tyr Ser Asn Phe Gln Ala Thr Thr Leu Arg Glu Leu Phe Lys Glu Glu
             20                  25                  30 aac cgc gcc gag aag tac acc ttc tcc gcg gct ggc ctc cac gtc gac     144
Asn Arg Ala Glu Lys Tyr Thr Phe Ser Ala Ala Gly Leu His Val Asp
         35                  40                  45 ctg tcg aag aat ctg ctt gac gac gcc acc ctc acc aag ctc ctt gca     192
Leu Ser Lys Asn Leu Leu Asp Asp Ala Thr Leu Thr Lys Leu Leu Ala
     50                  55                  60 ctg acc gaa gaa tct ggc ctt cgc gaa cgc att gac gcg atg ttt gcc     240
Leu Thr Glu Glu Ser Gly Leu Arg Glu Arg Ile Asp Ala Met Phe Ala
 65                  70                  75                  80 ggt gaa cac ctc aac aac acc gaa gac cgc gct gtc ctc cac acc gcg     288
Gly Glu His Leu Asn Asn Thr Glu Asp Arg Ala Val Leu His Thr Ala
                 85                  90                  95 ctg cgc ctt cct ccc gaa gct gat ctg tca gta gat ggc caa gat gtt     336
Leu Arg Leu Pro Pro Glu Ala Asp Leu Ser Val Asp Gly Gln Asp Val
```

|  |  |  |  |  |  |  |  |  |  |  |  |  |  |
|---|---|---|---|---|---|---|---|---|---|---|---|---|---|
|  | 100 |  |  |  | 105 |  |  |  |  | 110 |  |  |  |
| gct | gct | gat | gtc | cac | gaa | gtt | ttg | gga | cgc | atg | cgt | gac | ttc | gct | act | 384 |
| Ala | Ala | Asp | Val | His | Glu | Val | Leu | Gly | Arg | Met | Arg | Asp | Phe | Ala | Thr |
|  |  | 115 |  |  |  | 120 |  |  |  | 125 |  |  |  |
| gcg | ctg | cgc | tca | ggc | aac | tgg | ttg | gga | cac | acc | ggc | cac | acg | atc | aag | 432 |
| Ala | Leu | Arg | Ser | Gly | Asn | Trp | Leu | Gly | His | Thr | Gly | His | Thr | Ile | Lys |
| 130 |  |  |  | 135 |  |  |  | 140 |  |  |  |
| aag | atc | gtc | aac | att | ggt | atc | ggt | ggc | tct | gac | ctc | gga | cca | gcc | atg | 480 |
| Lys | Ile | Val | Asn | Ile | Gly | Ile | Gly | Gly | Ser | Asp | Leu | Gly | Pro | Ala | Met |
| 145 |  |  |  | 150 |  |  |  | 155 |  |  |  | 160 |
| gct | acg | aag | gct | ctg | cgt | gca | tac | gcg | acc | gct | ggt | atc | tca | gca | gaa | 528 |
| Ala | Thr | Lys | Ala | Leu | Arg | Ala | Tyr | Ala | Thr | Ala | Gly | Ile | Ser | Ala | Glu |
|  |  |  |  | 165 |  |  |  | 170 |  |  |  | 175 |
| ttc | gtc | tcc | aac | gtc | gac | cca | gca | gac | ctc | gtt | tct | gtg | ttg | gaa | gac | 576 |
| Phe | Val | Ser | Asn | Val | Asp | Pro | Ala | Asp | Leu | Val | Ser | Val | Leu | Glu | Asp |
|  |  |  | 180 |  |  |  | 185 |  |  |  | 190 |
| ctc | gat | gca | gaa | tcc | aca | ttg | ttc | gtg | atc | gct | tcg | aaa | act | ttt | acc | 624 |
| Leu | Asp | Ala | Glu | Ser | Thr | Leu | Phe | Val | Ile | Ala | Ser | Lys | Thr | Phe | Thr |
|  |  | 195 |  |  |  | 200 |  |  |  | 205 |  |  |  |
| acc | cag | gag | acg | ctg | tct | aac | gct | cgt | gca | gct | cgt | gct | tgg | ctg | gta | 672 |
| Thr | Gln | Glu | Thr | Leu | Ser | Asn | Ala | Arg | Ala | Ala | Arg | Ala | Trp | Leu | Val |
|  | 210 |  |  |  | 215 |  |  |  | 220 |  |  |  |
| gag | aag | ctc | ggt | gaa | gag | gct | gtc | gcg | aag | cat | ttc | gtc | gca | gtg | tcc | 720 |
| Glu | Lys | Leu | Gly | Glu | Glu | Ala | Val | Ala | Lys | His | Phe | Val | Ala | Val | Ser |
| 225 |  |  |  | 230 |  |  |  | 235 |  |  |  | 240 |
| acc | aat | gct | gaa | aag | gtc | gca | gag | ttc | ggt | atc | gac | acg | gac | aac | atg | 768 |
| Thr | Asn | Ala | Glu | Lys | Val | Ala | Glu | Phe | Gly | Ile | Asp | Thr | Asp | Asn | Met |
|  |  |  | 245 |  |  |  | 250 |  |  |  | 255 |
| ttc | ggc | ttc | tgg | gac | tgg | gtc | gga | ggt | cgt | tac | tcc | gtg | gac | tcc | gca | 816 |
| Phe | Gly | Phe | Trp | Asp | Trp | Val | Gly | Gly | Arg | Tyr | Ser | Val | Asp | Ser | Ala |
|  |  | 260 |  |  |  | 265 |  |  |  | 270 |  |  |  |
| gtt | ggt | ctt | tcc | ctc | atg | gca | gtg | atc | ggc | cct | cgc | gac | ttc | atg | cgt | 864 |
| Val | Gly | Leu | Ser | Leu | Met | Ala | Val | Ile | Gly | Pro | Arg | Asp | Phe | Met | Arg |
|  | 275 |  |  |  | 280 |  |  |  | 285 |  |  |  |
| ttc | ctc | ggt | gga | ttc | cac | gcg | atg | gat | gaa | cac | ttc | cgc | acc | acc | aag | 912 |
| Phe | Leu | Gly | Gly | Phe | His | Ala | Met | Asp | Glu | His | Phe | Arg | Thr | Thr | Lys |
|  | 290 |  |  |  | 295 |  |  |  | 300 |  |  |  |
| ttc | gaa | gag | aac | gtt | cca | atc | ttg | atg | gct | ctg | ctc | ggt | gtc | tgg | tac | 960 |
| Phe | Glu | Glu | Asn | Val | Pro | Ile | Leu | Met | Ala | Leu | Leu | Gly | Val | Trp | Tyr |
| 305 |  |  |  | 310 |  |  |  | 315 |  |  |  | 320 |
| tcc | gat | ttc | tat | ggt | gca | gaa | acc | cac | gct | gtc | cta | cct | tat | tcc | gag | 1008 |
| Ser | Asp | Phe | Tyr | Gly | Ala | Glu | Thr | His | Ala | Val | Leu | Pro | Tyr | Ser | Glu |
|  |  |  | 325 |  |  |  | 330 |  |  |  | 335 |
| gat | ctc | agc | cgt | ttt | gct | gct | tac | ctc | cag | cag | ctg | acc | atg | gaa | tca | 1056 |
| Asp | Leu | Ser | Arg | Phe | Ala | Ala | Tyr | Leu | Gln | Gln | Leu | Thr | Met | Glu | Ser |
|  |  | 340 |  |  |  | 345 |  |  |  | 350 |  |  |  |
| aac | ggc | aag | tca | gtc | cac | cgc | gac | ggc | tcc | cct | gtt | tcc | act | ggc | act | 1104 |
| Asn | Gly | Lys | Ser | Val | His | Arg | Asp | Gly | Ser | Pro | Val | Ser | Thr | Gly | Thr |
|  |  | 355 |  |  |  | 360 |  |  |  | 365 |  |  |  |
| ggc | gaa | att | tac | tgg | ggt | gag | cct | ggc | aca | aat | ggc | cag | cac | gct | ttc | 1152 |
| Gly | Glu | Ile | Tyr | Trp | Gly | Glu | Pro | Gly | Thr | Asn | Gly | Gln | His | Ala | Phe |
|  | 370 |  |  |  | 375 |  |  |  | 380 |  |  |  |
| ttc | cag | ctg | atc | cac | cag | ggc | act | cgc | ctt | gtt | cca | gct | gat | ttc | att | 1200 |
| Phe | Gln | Leu | Ile | His | Gln | Gly | Thr | Arg | Leu | Val | Pro | Ala | Asp | Phe | Ile |
| 385 |  |  |  | 390 |  |  |  | 395 |  |  |  | 400 |
| ggt | ttc | gct | cgt | cca | aag | cag | gat | ctt | cct | gcc | ggt | gag | cgc | acc | atg | 1248 |
| Gly | Phe | Ala | Arg | Pro | Lys | Gln | Asp | Leu | Pro | Ala | Gly | Glu | Arg | Thr | Met |
|  |  |  | 405 |  |  |  | 410 |  |  |  | 415 |
| cat | gac | ctt | ttg | atg | agc | aac | ttc | ttc | gca | cag | acc | aag | gtt | ttg | gct | 1296 |

```
                                                                    -continued His Asp Leu Leu Met Ser Asn Phe Phe Ala Gln Thr Lys Val Leu Ala
        420                 425                 430 ttc ggt aag aac gct gaa gag atc gct gcg gaa ggt gtc gca cct gag    1344
Phe Gly Lys Asn Ala Glu Glu Ile Ala Ala Glu Gly Val Ala Pro Glu
            435                 440                 445 ctg gtc aac cac aag gtc atg cca ggt aat cgc cca acc acc acc att    1392
Leu Val Asn His Lys Val Met Pro Gly Asn Arg Pro Thr Thr Thr Ile
450                 455                 460 ttg gcg gag gaa ctt acc cct tct att ctc ggt gcg ttg atc gct ttg    1440
Leu Ala Glu Glu Leu Thr Pro Ser Ile Leu Gly Ala Leu Ile Ala Leu
465                 470                 475                 480 tac gaa cac atc gtg atg gtt cag ggc gtg att tgg gac atc aac tcc    1488
Tyr Glu His Ile Val Met Val Gln Gly Val Ile Trp Asp Ile Asn Ser
                    485                 490                 495 ttc gac caa tgg ggt gtt gaa ctg ggc aaa cag cag gca aat gac ctc    1536
Phe Asp Gln Trp Gly Val Glu Leu Gly Lys Gln Gln Ala Asn Asp Leu
            500                 505                 510 gct ccg gct gtc tct ggt gaa gag gat gtt gac tcg gga gat tct tcc    1584
Ala Pro Ala Val Ser Gly Glu Glu Asp Val Asp Ser Gly Asp Ser Ser
        515                 520                 525 act gat tca ctg att aag tgg tac cgc gca aat agg tag                 1623
Thr Asp Ser Leu Ile Lys Trp Tyr Arg Ala Asn Arg
    530                 535                 540

<210> SEQ ID NO 2
<211> LENGTH: 540
<212> TYPE: PRT
<213> ORGANISM: Corynebacterium glutamicum

<400> SEQUENCE: 2

Met Ala Asp Ile Ser Thr Thr Gln Ala Trp Gln Asp Leu Thr Asp His
1               5                   10                  15

Tyr Ser Asn Phe Gln Ala Thr Thr Leu Arg Glu Leu Phe Lys Glu Glu
            20                  25                  30

Asn Arg Ala Glu Lys Tyr Thr Phe Ser Ala Ala Gly Leu His Val Asp
        35                  40                  45

Leu Ser Lys Asn Leu Leu Asp Asp Ala Thr Leu Thr Lys Leu Leu Ala
    50                  55                  60

Leu Thr Glu Glu Ser Gly Leu Arg Glu Arg Ile Asp Ala Met Phe Ala
65                  70                  75                  80

Gly Glu His Leu Asn Asn Thr Glu Asp Arg Ala Val Leu His Thr Ala
                85                  90                  95

Leu Arg Leu Pro Pro Glu Ala Asp Leu Ser Val Asp Gly Gln Asp Val
            100                 105                 110

Ala Ala Asp Val His Glu Val Leu Gly Arg Met Arg Asp Phe Ala Thr
        115                 120                 125

Ala Leu Arg Ser Gly Asn Trp Leu Gly His Thr Gly His Thr Ile Lys
    130                 135                 140

Lys Ile Val Asn Ile Gly Ile Gly Gly Ser Asp Leu Gly Pro Ala Met
145                 150                 155                 160

Ala Thr Lys Ala Leu Arg Ala Tyr Ala Thr Ala Gly Ile Ser Ala Glu
                165                 170                 175

Phe Val Ser Asn Val Asp Pro Ala Asp Leu Val Ser Val Leu Glu Asp
            180                 185                 190

Leu Asp Ala Glu Ser Thr Leu Phe Val Ile Ala Ser Lys Thr Phe Thr
        195                 200                 205

Thr Gln Glu Thr Leu Ser Asn Ala Arg Ala Ala Arg Ala Trp Leu Val
```

| | | | | | | | | | | | |
|---|---|---|---|---|---|---|---|---|---|---|---|
| | 210 | | | | 215 | | | | 220 | | |
| Glu 225 | Lys | Leu | Gly | Glu 230 | Glu | Ala | Val | Ala 235 | Lys | His | Phe | Val | Ala | Val 240 | Ser |

```
            210                 215                 220
Glu Lys Leu Gly Glu Glu Ala Val Ala Lys His Phe Val Ala Val Ser
225                 230                 235                 240

Thr Asn Ala Glu Lys Val Ala Glu Phe Gly Ile Asp Thr Asp Asn Met
                245                 250                 255

Phe Gly Phe Trp Asp Trp Val Gly Gly Arg Tyr Ser Val Asp Ser Ala
                260                 265                 270

Val Gly Leu Ser Leu Met Ala Val Ile Gly Pro Arg Asp Phe Met Arg
            275                 280                 285

Phe Leu Gly Gly Phe His Ala Met Asp Glu His Phe Arg Thr Thr Lys
290                 295                 300

Phe Glu Glu Asn Val Pro Ile Leu Met Ala Leu Leu Gly Val Trp Tyr
305                 310                 315                 320

Ser Asp Phe Tyr Gly Ala Glu Thr His Ala Val Leu Pro Tyr Ser Glu
                325                 330                 335

Asp Leu Ser Arg Phe Ala Ala Tyr Leu Gln Gln Leu Thr Met Glu Ser
                340                 345                 350

Asn Gly Lys Ser Val His Arg Asp Gly Ser Pro Val Ser Thr Gly Thr
            355                 360                 365

Gly Glu Ile Tyr Trp Gly Glu Pro Gly Thr Asn Gly Gln His Ala Phe
370                 375                 380

Phe Gln Leu Ile His Gln Gly Thr Arg Leu Val Pro Ala Asp Phe Ile
385                 390                 395                 400

Gly Phe Ala Arg Pro Lys Gln Asp Leu Pro Ala Gly Glu Arg Thr Met
                405                 410                 415

His Asp Leu Leu Met Ser Asn Phe Phe Ala Gln Thr Lys Val Leu Ala
                420                 425                 430

Phe Gly Lys Asn Ala Glu Glu Ile Ala Ala Glu Gly Val Ala Pro Glu
            435                 440                 445

Leu Val Asn His Lys Val Met Pro Gly Asn Arg Pro Thr Thr Thr Ile
450                 455                 460

Leu Ala Glu Glu Leu Thr Pro Ser Ile Leu Gly Ala Leu Ile Ala Leu
465                 470                 475                 480

Tyr Glu His Ile Val Met Val Gln Gly Val Ile Trp Asp Ile Asn Ser
                485                 490                 495

Phe Asp Gln Trp Gly Val Glu Leu Gly Lys Gln Gln Ala Asn Asp Leu
                500                 505                 510

Ala Pro Ala Val Ser Gly Glu Glu Asp Val Asp Ser Gly Asp Ser Ser
            515                 520                 525

Thr Asp Ser Leu Ile Lys Trp Tyr Arg Ala Asn Arg
530                 535                 540
```

<210> SEQ ID NO 3
<211> LENGTH: 25
<212> TYPE: DNA
<213> ORGANISM: Corynebacterium glutamicum

<400> SEQUENCE: 3
gctgatgtcc acgaagcttt gggac                                          25

<210> SEQ ID NO 4
<211> LENGTH: 25
<212> TYPE: DNA
<213> ORGANISM: Corynebacterium glutamicum

```
<400> SEQUENCE: 4
gctgagaacc ttggaataag gtagg                                          25
```